US006620149B1

(12) United States Patent
Lenz et al.

(10) Patent No.: US 6,620,149 B1
(45) Date of Patent: Sep. 16, 2003

(54) COREWIRE SECUREMENT SYSTEM (75) Inventors: Jason T. Lenz, Maplewood, MN (US); Mirna A. Slayhi, Minneapolis, MN (US); Loren J. Simer, Jr., Minnetonka, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 350 days.

(21) Appl. No.: 09/680,809

(22) Filed: Oct. 5, 2000

(51) Int. Cl.$^7$ .......................... A61M 25/00; A61M 5/00
(52) U.S. Cl. ....................... 604/524; 604/264; 604/523; 604/533
(58) Field of Search ................................. 606/194, 192; 604/30, 33, 99.01–99.04, 103.01, 164.13, 165.01, 165.02, 167.01, 167.03, 246, 249, 247, 264, 523, 528, 533, 537, 284, 905, 164.01, 164.07, 164.12, 165.04; 600/433–435, 585; 267/166, 167, 168

(56) References Cited

U.S. PATENT DOCUMENTS

| | | | | |
|---|---|---|---|---|
| 4,512,766 A | * | 4/1985 | Vailancourt | 604/167.03 |
| 4,559,046 A | * | 12/1985 | Groshong et al. | 604/524 |
| 4,737,153 A | * | 4/1988 | Shimamura et al. | 604/526 |
| 4,875,481 A | * | 10/1989 | Higgins | 606/194 |
| 4,940,062 A | * | 7/1990 | Hampton et al. | 600/585 |
| 4,976,689 A | | 12/1990 | Buchbinder et al. | 604/95 |
| 5,034,001 A | | 7/1991 | Garrison et al. | 604/53 |
| 5,035,686 A | | 7/1991 | Crittenden et al. | 604/96 |
| 5,156,594 A | | 10/1992 | Keith | 604/96 |
| 5,163,903 A | | 11/1992 | Crittenden et al. | 604/96 |
| 5,167,239 A | * | 12/1992 | Cohen et al. | 600/585 |
| 5,176,637 A | | 1/1993 | Sagae | |
| 5,180,368 A | | 1/1993 | Garrison | 604/104 |
| 5,242,430 A | * | 9/1993 | Arenas et al. | 604/523 |
| 5,250,034 A | * | 10/1993 | Appling et al. | 604/523 |

(List continued on next page.)

FOREIGN PATENT DOCUMENTS

WO    WO 9713455 A1 * 4/1997 ............ A61B/5/00

*Primary Examiner*—Michael J. Milano
*Assistant Examiner*—Jessica R Baxter
(74) *Attorney, Agent, or Firm*—Crompton, Seager & Tufte LLC (57) ABSTRACT

A catheter for use in vasculature or other lumen within body structures includes a shaft formed from an elongated polymeric flexible tube. A metallic tube may be bound to the distal end of this tube. A thinner, more flexible tube may be attached to the distal end of a metallic tube. The two plastic tubes, together with any metallic tube define a lumen for providing communication with an angioplasty balloon or with a body lumen at the distal end of the catheter. A catheter may include a core member to facilitate moving the catheter through a lumen, and to reduce the likelihood that the catheter will kink or bend improperly. This metallic core member extends from the hub to some point distal on the catheter, and may extend to the distal tip of the catheter. The distal end of a catheter balloon may be secured to the core member during manufacture of the catheter. The core member has a zigzagged or helix shape at the proximal end which is friction fit into the hub lumen, and may have a pointed tip that embeds in the hub inner wall. During manufacture, the core member can be secured within the hub with reduced reliance on adhesives or molding of the core member within the hub body. The core member may be secured within the hub by being press fit into the hub lumen. The catheter is more easily manufactured, and has an increased volume and reduced obstruction by adhesive in comparison with other methods of securing the core member.

15 Claims, 3 Drawing Sheets

U.S. PATENT DOCUMENTS

| | | | |
|---|---|---|---|
| 5,263,963 A | 11/1993 | Garrison et al. | 606/198 |
| 5,290,247 A | 3/1994 | Crittenden | 604/171 |
| 5,364,354 A | 11/1994 | Walker et al. | 604/96 |
| 5,425,711 A | 6/1995 | Ressemann et al. | 604/96 |
| 5,489,271 A | 2/1996 | Andersen | 604/102 |
| 5,490,837 A | 2/1996 | Blaeser et al. | 604/96 |
| 5,497,782 A | 3/1996 | Fugoso | |
| 5,531,690 A | 7/1996 | Solar | 604/102 |
| 5,549,553 A | 8/1996 | Ressemann et al. | 604/96 |
| 5,571,087 A | 11/1996 | Ressemann et al. | 604/96 |
| 5,658,251 A | 8/1997 | Ressemann et al. | 604/102 |
| 5,718,683 A | 2/1998 | Ressemann et al. | 604/96 |
| 5,720,724 A | 2/1998 | Ressemann et al. | 604/96 |
| 5,752,932 A | 5/1998 | Ellis et al. | 604/96 |
| 5,755,685 A | 5/1998 | Andersen | 604/53 |
| 5,827,242 A | 10/1998 | Follmer et al. | |
| 5,919,164 A | 7/1999 | Andersen | 604/102 |
| 5,921,958 A | 7/1999 | Ressemann et al. | 604/96 |
| 5,947,927 A | 9/1999 | Mertens | 604/96 |
| 5,980,484 A | 11/1999 | Ressemann et al. | 604/96 |
| 5,997,487 A | 12/1999 | Kolehmainen et al. | 600/585 |
| 6,004,291 A | 12/1999 | Ressemann et al. | 604/96 |
| 6,027,461 A | 2/2000 | Walker et al. | 600/585 |
| 6,030,407 A | 2/2000 | Eidenschink | 606/198 |
| 6,033,381 A | 3/2000 | Kontos | 604/96 |
| 6,068,610 A | 5/2000 | Ellis et al. | 604/96 |
| 6,068,622 A | 5/2000 | Sater et al. | 604/524 |
| 6,283,950 B1 * | 9/2001 | Appling | 604/523 |
| 6,308,090 B1 * | 10/2001 | Tu et al. | 600/585 |
| 6,368,302 B1 * | 4/2002 | Fitzmaurice et al. | 604/528 |
| 6,371,928 B1 * | 4/2002 | Mcfann et al. | 600/585 |
| 6,428,489 B1 * | 8/2002 | Jacobsen et al. | 600/585 |

* cited by examiner

COREWIRE SECUREMENT SYSTEM

BACKGROUND OF THE INVENTION

The present invention relates to the field of catheterization of lumen within the human body, particularly vasculature. Even more particularly, the invention will have application to the manufacture and construction of balloon catheters used in angioplasty.

Angioplasty procedures have gained wide acceptance as an efficient and effective method for treating certain types of vascular diseases. In particular, angioplasty is widely used for stenoses in the coronary arteries, although it is also used for the treatment of stenoses in other parts of the vascular system. The use of core members to provide rigidity and pushability for catheters is well known, and the incorporation of such core members is discussed, for example, in U.S. Pat. No. 5,921,958, entitled Intravascular Catheter with Distal Tip Guide Wire Lumen, which is hereby incorporated by reference.

The most widely used form of angioplasty makes use of a dilatation balloon catheter to treat a stenosis and thereby reestablish an acceptable blood flow through the artery. The dilatation catheter includes an elongated tubular shaft and an inflatable balloon carried at a distal end of the shaft. In operation, the catheter is inserted through a guide catheter which has been previously introduced into a patient's vascular system from a location remote from the heart (e.g., femoral artery). The proximal end of the guide catheter remains outside the patient while the distal end of the guide catheter is positioned at the coronary artery ostium. A dilatation catheter is introduced into the proximal end of the guiding catheter and advanced to the distal end of the guide catheter. Then, by using fluoroscopy, the physician guides the dilatation catheter the remaining distance through the vascular system until the balloon is positioned across the stenosis.

The balloon is then inflated by supplying fluid under pressure, through an inflation lumen in the catheter, to the balloon. The inflation of the balloon causes a widening of the lumen of the artery to reestablish acceptable blood flow through the artery. After a short inflation period (e.g., 30–90 seconds), the balloon is deflated and the arterial treatment evaluated to determine whether the procedure has reestablished an acceptable blood flow. The evaluation is conducted by introducing a radiopaque dye solution into the artery via the guiding catheter, and then observing the dye flow using fluoroscopy. If necessary, the dilatation procedure is repeated with the catheter balloon being re-inflated. In procedures in the peripheral vessels (vessels other than coronary vessels), a guide catheter may not always be used.

The placement of the dilatation balloon across a stenosis in a coronary artery can be a difficult procedure. Movement of the elongated dilatation balloon catheter (e.g., 135 cm) is achieved by manual manipulation of its proximal end outside the patient. The ability of a catheter to bend and advance through the vasculature is commonly referred to as the "trackability" of the catheter. "Pushability" refers to the ability of the catheter to transmit the longitudinal forces applied by the physician along the catheter shaft to advance the distal end of the catheter through a coronary artery to and across the stenosis. Preferably, a catheter has a low profile, and is relatively trackable and pushable.

One common type of dilatation catheter has a guide wire lumen extending through the catheter so that a guide wire can be used to establish the path through the stenosis. The dilatation catheter can then be advanced over the guide wire until the balloon on the catheter is positioned within the stenosis.

In a catheter design where the guide wire does not extend through the catheter balloon, it is important that the catheter structure provide sufficient rigidity along the catheter shaft and through the balloon (all the way to the distal tip of the catheter where the guide wire lumen is located), so that the catheter has the necessary pushability. A core member helps provide this rigidity and pushability. On some catheters, the core member may provide axial rigidity to the entire distal shaft section. On many catheters, particularly balloon catheters, the core member serves a strain relief function as well. The core member reduces kinking of the catheter lumen, such as the inflation lumen in a balloon catheter, which might otherwise occur due to a change in flexibility between a relatively stiff section of tubing, to that of a relatively flexible distal shaft portion.

Core members are typically affixed at the proximal end of the catheter to the catheter hub or manifold. They are affixed either by being embedded in the material from which the hub is formed at the time the hub is manufactured, being affixed with a solder or braze, or being embedded in a mass or glob of cyanoacrylate, epoxy, resin, or other adhesive affixed to the inner wall of the hub. These latter methods tend to complicate the manufacture of the catheter, as either the core member must be incorporated into the hub molding or machining, or else the adhesive must be added to the hub after the hub is formed. Correct placement of the core member adhesive within the hub lumen is a relatively delicate manufacturing procedure which may lead to errors and rejection of catheters under quality control standards. Furthermore, some of these methods of affixing the core member may not sufficiently bond the core member to the hub for all applications or situations.

SUMMARY OF THE INVENTION

The present invention pertains to an intralumenal catheter with a core member extending from a proximal hub and through some portion of a shaft distal to the hub. Fixation of the core member into the hub lumen is accomplished in a way that is easier to manufacture than prior methods of securing the core member. The present invention may increase the reliability of the production process, in addition to making the core member more securely fixed in the hub. A catheter of the present invention may also have an inflatable angioplasty balloon, or other devices for reducing or ablating a stenosis, such as an atherectomy-type cutter, a laser device, a water jet device, or sonic or ultrasonic therapeutic devices. The present invention may also be used with other interoperative devices such as drug delivery devices, ultrasonic imaging devices and perfusion devices.

One embodiment of the present invention is a catheter with a flexible, elongate tubular shaft. This shaft has a lumen throughout, and has a proximal and a distal end. A hub with an inner lumen is attached to the proximal end of the shaft. A core member, which runs though at least a portion of the catheter shaft, extends proximally into the hub lumen, and is secured within the lumen. While the core member is substantially in the center of the lumen when entering the distal end of the hub, proximally to this the core member contacts the inner wall of the hub lumen of the hub at two or more points, traversing the hub lumen between points of contact with the inner wall of the hub.

Moving along the core member from a distal opening of the hub to a proximal opening of the hub, the core member at some point is angled so as to gradually extend out from the center of the lumen and contact the inner wall of the hub lumen. After contacting the inner wall of the lumen, the core member is again angled so as to extend to another point on the hub lumen inner wall, such point located proximally from the first point of contact with the hub lumen, but not located on a longitudinal line on the hub lumen inner wall that crosses through the first point of contact. In reaching the second point of contact with the hub inner wall, therefore, the core member may cross substantially over the center of the hub lumen when viewed radially. The core member may then be again angled to contact yet another proximally located point on the hub inner wall. This point, proximal to the first and second points of contact, may be on a longitudinal line on the hub inner wall that crosses through the first point ofcontact, or may be another point on the hub lumen inner wall that is closer to the proximal end of the hub than were the prior points of contact.

The core member is bent or formed so as to zigzag within the lumen of the hub, contacting the walls of the hub in at least two points. The core member is bent or formed in a manner that, if the core member is not in the hub, the core member will spring or expand to a zigzag shape that is slightly wider than the hub lumen, so that upon placement of the core member within the hub lumen, the core member is tension-fit or friction-fit within the hub lumen. In a preferred embodiment of the present invention, the tension caused by the tendency of the core member to expand is such to provide a snug fit and to secure the core member within the hub. In this embodiment of the present invention, the core member may be formed into the desired angled shape using multiple methods or techniques. The core member may be molded, cast, or rolled in the desired shape, or it may be bent or folded after the initial formation of the core member. In either case, in a preferred embodiment, the width of the angled portion of the core member, prior to insertion, is greater than the inner diameter of the hub lumen at least to an extent necessary so that the core member will be secured within the hub when placed in the hub.

When one embodiment of the present invention is viewed axially, i.e., through the hub lumen, the core member zigzag pattern will lie substantially on a plane. In other words, the points of contact between the core member and the hub inner wall lie substantially along two opposite longitudinal lines on the inner wall of the hub lumen. Viewing the core member axially, the angled portions of the core member other than those closest to the viewer may be blocked by the core member angles which are closest to the viewer. However, other embodiments of the present invention are possible, including an embodiment in which the core member, either proximally or distally to a point of contact with the hub inner wall, may traverse the inner hub lumen to make contact with the hub inner wall at a point which is not located on a longitudinal line on the inner wall of the hub which is directly opposite, vis-à-vis the central lumen axis, a longitudinal line passing through a prior point of contact. Alternately stated, when the core member is viewed axially, or "end on" through the hub lumen, the core member may appear to form the shape of a star, an "N" shape, or any other shape or irregular pattern not reflecting formation on a single plane. In an alternative embodiment incorporating a non-planar anchor configuration, the core member may be formed into a conical or cylindrical helix, contacting the inner wall of the hub more or less continuously along a length of the core member anchor section.

In contrast to core member securement systems of the prior art, the present invention provides for improved and simplified manufacturing processes, and does not require that the core member be molded into the hub wall, or glued to the hub wall. Morever, unlike the present invention, prior methods of core member securement may significantly impede flow of fluid through the hub lumen when the hub lumen is needed for fluid communication.

In a preferred embodiment of the present invention, a catheter has a core wire anchored in accordance with the above embodiment, but in addition, the hub lumen is in fluid communication with the shaft lumen, allowing for delivery of balloon inflation media, such as saline, or other fluids, dyes, or pharmacological material that must be delivered to or through the distal end of the catheter. The catheter may also be capable of conveying fluid material from the distal to the proximal end where the necessary pressure differential, i.e., suction, holds. An embodiment of the present invention incorporates a flexible strain relief sheathing, surrounding the catheter shaft distal to the area of the hub, but in close proximity to the hub, to further prevent crimping and to help prevent a degree of bending that may damage the shaft in the area where it meets the hub. The strain relief is flexible, but not as flexible as the shaft in the area distal to the hub. In a preferred embodiment, the flexible strain relief becomes more difficult to flex as it is flexed, and becomes very difficult to flex as it approaches a degree of flexion wherein the shaft surrounded by the strain relief is near its limit of flexion, i.e., at a point where it is in danger of kinking or folding.

An embodiment of the present invention discloses a method of manufacture and attachment of the core member within the hubs. Under this embodiment, the core member is first formed into a zigzag or spiral pattern disclosed in previously discussed embodiments of the invention. In various embodiments, this formation may be effected by molding the core member into the desired shape, or by bending or pressing the core member to the desired shape, including by the use of a peg template, a crimping press, or another suitable device. Following the formation of the core member into a zigzag or spiral pattern, the so-formed end of the core member is inserted and press fit into the hub lumen with sufficient force to secure the core member within the hub lumen, but in a preferred embodiment, without such force that will substantially bend or crimp the core member further. In an alternative embodiment of the present invention, the distal end of the core member may be pushed though the proximal end of the hub lumen, and after the distal end of the core member is accessible at the distal end of the hub lumen, the core member may be pulled through the hub lumen until the angled proximal end of the core member becomes fixed within the hub lumen. Preferably, the proximal tip of the core member will be pointed so as to embed into the inner wall of the hub lumen, thus further securing the core member within the hub.

BRIEF DESCRIPTION OF THE DRAWINGS

The invention will be further described with reference to the accompanying drawings.

DETAILED DESCRIPTION OF THE PREFERRED EMBODIMENTS

Figure 1:
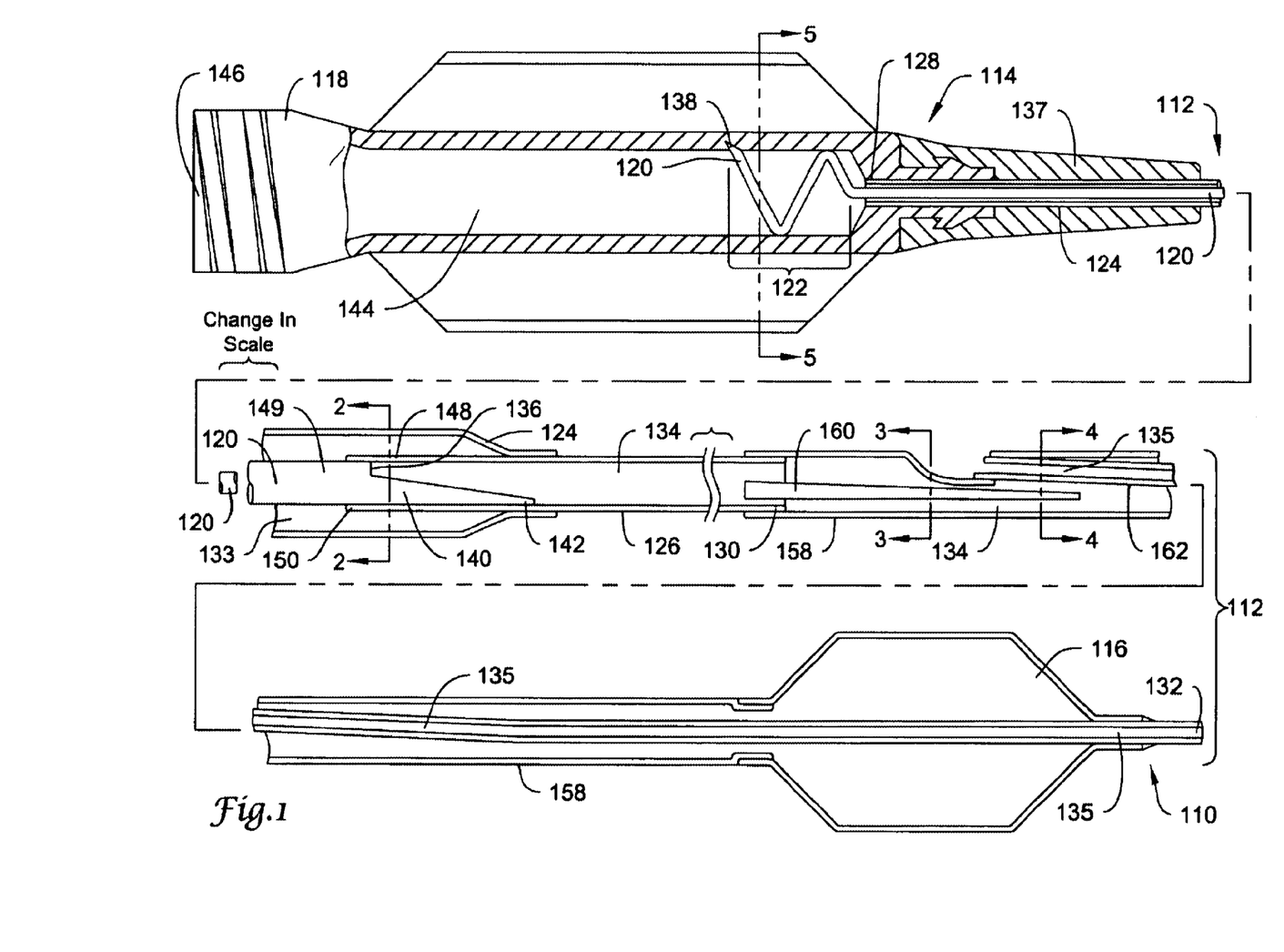
FIG. 1 is a cross-sectional view of a catheter of the present invention.

The present invention may be embodied in an intraluminal catheter such as that of FIG. 1 illustrating an angioplasty dilatation balloon catheter, generally at 110. The catheter 110 has a shaft indicated generally as shaft 112 which has a hub 114 on its proximal end. The catheter may have an inflatable angioplasty balloon 116 on its distal end, as depicted. Although the inventive catheter described and illustrated herein is shown in reference to a balloon dilatation catheter for stenosis treatment, other stenosis-reducing mechanisms, or other therapeutic or diagnostic devices may also be disposed on the distal end of the catheter shaft 112.

The hub 114 may have a mating member 118, e.g., a luer connector as shown. A metallic core member 120 is fixed within the hub 114 of the catheter 110. The hub 114 contains within a zigzag anchoring structure 122 of core member 120. Core member 120 extends longitudinally from hub 114, and extends through tubular shaft 112 of the catheter 110 to any extent as required by the catheter's specific application.

In a preferred embodiment, shaft 112 includes a first tubular segment 124, which is a relatively flexible polymeric tubular shaft. Preferably, tubular segment 124 is formed as a thin-walled, high-strength flexible polymeric tube. In a preferred embodiment, a metallic tube 126 is also included in the device, such metallic tube preferably being a stainless steel tube structure, which is commonly referred to as hypodermic tub ing or hypotube. One suitable type of hypotube has a nominal outer diameter of approximately 0.025 in. and a nominal inner diameter of approximately 0.020 inches. Metallic tubing 126 may be bonded to the distal end of the polymeric tubular shaft 124.

In an illustrative embodiment and as depicted in FIG. 1, core member 120 extends through a proximal polymeric shaft 124, and into a metallic tube 126 but not to the distal end 130 of the metallic tube 126. In such an embodiment, an additional stiffening wire 160 may be provided at the distal end of metallic tube 126 in order to prevent kinking in the transition between metallic tube 126 and distal flexible shaft 158. The core member 120 may alternatively extend throughout the catheter inner lumen to the distal end 130 of any metallic tube 126, and may further extend to an area of a balloon 116, or to the distal tip 132 of the catheter 110. The illustrative embodiment of FIG. 1, the catheter 110 which includes a balloon 116, has an inflation lumen to provide a path through which inflation fluid is provided to and from the balloon 116. As tubular structures, the interiors of the tubular segment 124, and any metallic tube 126, are preferably hollow, and thus together define an inflation lumen 133 and 134, extending from a proximal end 128 of tubular segment 124, the inflation lumen of which is indicated by 133, through to a distal end 130 of metallic tube 126, preferably continuing into any distal flexible segments. The present invention may also have a guide wire lumen 135 within the distal portion of the catheter, or in other lengths of the catheter distal to the core member 120 secured in the hub.

The core member 120 provides two related functions. First, it provides axial or column strength to the proximal shaft section 124. Second, the core member 120 minimizes kinking of the proximal shaft section 124. (As discussed above, the polymeric tube 124 defining the first tubular segment is preferably relatively flexible in the absence of the core member 120.)

Relatively stiff catheter sections are defined at both ends of the proximal shaft section 124 by the metallic tube 126 at the distal end and by the catheter hub 114 at the proximal end 128. Without the core member 120 extending therebetween, such a configuration might tend to buckle or bend in the relatively flexible area 124 as an attempt is made to advance the catheter 110 through the patient's vasculature. Responsiveness of the catheter would thus be substantially diminished. A strain relief member 137 may also be provided in order to prevent kinking of proximal shaft section 124.

Further, the catheter 110 might tend to kink adjacent the shaft transition from the flexible polymeric tube 124 to the hypotube 126, or adjacent the transition between the hub 114 to the relatively more flexible proximal shaft section 124. The core member 120 is a structural member which increases the stiffness of the proximal shaft section 124. The core member 120 is less stiff (or has less axial strength) than the hub 114, and than a metallic tube 126, but is more stiff than the polymeric proximal shaft 124. The core member 120, however, is configured to be more trackable than the metallic tube 126. Thus, the combination proximal shaft section, polymeric tube 124 and core member 120 will preferably be more pushable than the polymeric tubular segment 124 alone, and yet more trackable than the metallic tube 126. The core member 120 preferably provides a relatively constant stiffness along its length, but alternatively may provide varying flexibility along its length such that its flexibility increases in the distal direction in a manner similar to that shown in stiffening wire 160. Where a distal stiffening wire 160 is provided, as illustrated in FIG. 1, stiffening wire 160 may provide varying flexibility along its length by one or more distal reductions in its outer diameter (formed, e.g., by ground tapers).

In a representative embodiment of the present invention, at its proximal end 138, the core member 120 may have a diameter of approximately 0.020 inches, while adjacent its distal end 140, the core member 120 may have a diameter of approximately 0.0055 inches and be gradually flattened along its distal 0.150 inches to form a ribbon 142 of 0.002 inches by 0.012 inches that is 0.03 to 0.05 inches long.

The core member 120 is preferably formed of a high strength stainless steel or other high strength alloy such as 17-7PH stainless, 18-8PH stainless, and 300 or 400 Series stainless steel. In one embodiment, the core member 120 is formed from a core wire of Type 304 stainless steel and manufactured by centerless grinding. While typically, the anchor portion of the core member will be formed by bending the core member into the desired configuration after manufacture, other embodiments are possible, including molding the core member in the desired shape at the time of formation of the core member out of molten alloy. While in the preferred embodiment, the anchor 122 of the core member 120 will be constructed of a uniform material with that of the core member 120 as a whole, other embodiments within the scope of the invention are possible, such as a configuration by which the anchor portion is constructed of a different alloy or material, and fused or joined fixedly with the remainder of the core member at some point distal of the anchor assembly 122.

In a preferred embodiment, the proximal end 138 of the core member 120 is received within the hub lumen 144 and anchored therein by a suitable process of bending the core member into a zigzag shape which, prior to placement within the hub lumen, is wider than the diameter of the inside lumen of the hub. The zigzag anchor portion 122 of the core member 120 may then be press fit or otherwise inserted into the hub lumen 144, until the core member 120 is anchored. If convenient in the manufacture of the catheter, the core member 120 may be inserted distal end 142 first into the proximal end 146 of the hub, and fed or pulled through the hub 114 until the core member anchor 122 is contained within and affixed to the walls of the hub lumen 144. In order to further secure the core 10 member anchor 122 within hub inside lumen 144, and as depicted in FIG. 1, the proximal end or tip 138 of core member 120 is preferably ground or otherwise formed into a sharp or pointed tip, which may at least partially dig into or embed into the plastic inner wall of hub lumen 144. This point formed into core member proximal tip 138 may have a centered point, but preferably is formed by grinding a planar surface into the tip 138 that is not perpendicular to the center axis of the core member material. The embedding of pointed tip 138 acts to prevent movement of the core member anchor 122 relative to hub lumen 144. In a preferred embodiment, the core member tip 138 is ground to an angle of about thirty degrees (30°) relative to a straight cut in the core member tip that is perpendicular to the radial axis of material making up the core member 120 at the tip 138.

In an alternative embodiment, the proximal portion of the core member 120 may be formed into a spiral, or a cylindrical or conical helix shaped core member anchor 122. In this embodiment, a length of core wire anchor 122 may be in substantially continuous contact with the inside lumen 144 of hub 114. Preferably, in this embodiment, the helix core member anchor 122 is biased to expand when in place in inside lumen 144, thus securing core member anchor 122 within hub 114. This embodiment may be constructed by the formation of a helix that is slightly larger than the hub lumen 144, and which must be compressed somewhat in order to be placed within hub lumen 144. In a representative embodiment of this invention, this slightly oversized helix will aid in retention of core member anchor 122 within hub lumen 144.

The length, angles, circumference and/or spacing of the core member anchor pattern 122 will vary depending upon the length of the proximal polymeric shaft section 124 for the catheter 110 (which may vary within a range of about 25 cm to over 35 cm, depending upon intended use), and upon the length of any metallic shaft 126 included. As seen in FIG. 1, the proximal end 138 of the core member 120 is offset from the axis of the hub lumen 144, but assumes a generally central axial alignment proximally of the connection of the core member 120 to a metallic tube 126.

Figure 2:
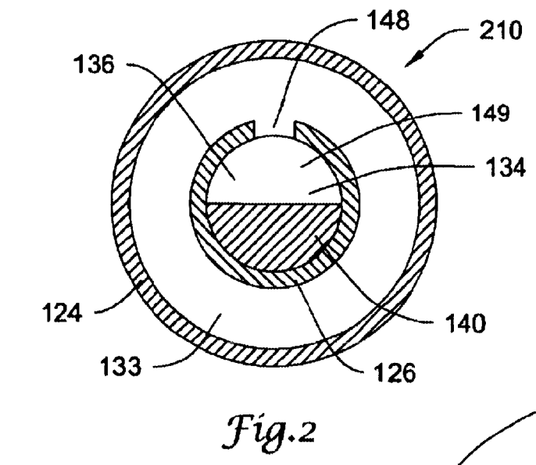
FIG. 2 is an axial cross-sectional view of the shaft of the catheter of FIG. 1, along line 2—2 of FIG. 1.

Tubular segment 124 is suitably flexible, despite the presence of the core member 120, due to the polymeric material from which tubular segment 124 is fabricated. Where fluid communication is required between the polymeric flexible shaft segment 124 and a hypotube or metallic tubular segment 126, a preferred embodiment includes a slot in the top of the hypotube at 148. A cross sectional view of this slot, along the line 2—2 in FIG. 1, is shown in FIG. 2. The cross-section is shown generally at 210. The slot, 148, is cut into the metallic tube 126. The axial half of the core member closest to the slot 148 is indicated by 140. This portion of the core member stops relatively abruptly at some point proximate to the slot 140, as shown in the transition of core member segment 149 to core member segment 140 in FIG. 1. The cross-section plane of FIG. 2 is distal this transition. In FIG. 1, it is shown that while the core member 120 blocks substantially all of the lumen of the metallic tube 126 at the proximal end 150 of the metallic tube, the core member has a relatively abrupt decrease in its thickness at 136, where approximately half of the thickness of core member 120 is eliminated for the core member 140 distal to transition 136.

As shown in FIG. 2, this step-down in the height of the core member 120 allows for fluid communication throughout the lumen, because the slot 148 extends over the core member 140 of the decreased thickness. Fluids may pass through the lumen of the polymeric proximal tube 133 except where core member 120 occupies the space, substantially in the center of the proximal polymeric tube 124 lumen 154. From the lumen 133 of the proximal polymeric tube 124, fluids may pass through slot 148, and into the lumen 156 of metallic tube 126. Fluids are not blocked by the core member 120 distal to the reduction in height of the core member at 136. In an illustrative embodiment, the slot is approximately 0.008 inches wide, and 1.5 mm long, such slot extending approximately 0.5 mm distal to the step down in thickness of the core member 120 at 136 in FIG. 1.

The thin-walled polymeric tube structure of tube 124, as stiffened by the core member 120, is stiff enough to provide the desired pushability, yet allows for a relatively small profile shaft of the catheter 1110. The high column strength and thickness of the polymeric shaft 124, as reinforced by the core member 120, as well as any metallic tube 126 included, give the catheter improved responsiveness. However, the stiffness of such a tube, and any metallic tube 126 that may be included, may not sufficiently allow the catheter to properly negotiate the coronary arteries or the arch of the aorta. Thus, in a preferred embodiment, a third tubular distal segment 158 may be provided that is more flexible than either the first polymeric tubular segment 124 or a metallic segment 126. This distal tubular section 158, if included, may be fixed by welding, adhesive, or other bonding on the metallic tubular segment 126.

As shown in FIG. 1, the distal tubular segment 157 may also have a guide wire lumen 135 so that a guide wire may be used to maneuver the catheter into the desired vessel of the body. The distal flexible tubular segment 158 may have a distal stiffening member 160 that is not affixed to either the hub 114, or to the hub-anchored core member 120. This distal stiffening member 160 can help to provide the catheter 110 with sufficient pushability in its distal catheter section from a hypotube shaft 126 to a distal guide wire lumen 135 on the distal tip of the catheter 110. This distal stiffening wire 160, if included, would preferably extend both distally and proximally from a transition between a metallic tube 126 and a distal flexible shaft, 158. The distal stiffening wire 160 provides a more gradual transition between the relatively stiff metallic shaft 126 and the relatively flexible distal section of the catheter shaft 158. The distal shaft section 158 will be afforded good pushability while still being quite trackable.

Figure 3:
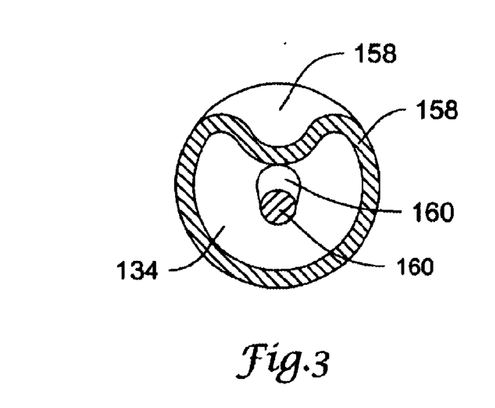
FIG. 3 is an axial cross-sectional view of another portion of the shaft of the catheter of FIG 1, along line 3—3 of FIG. 1.
Figure 4:
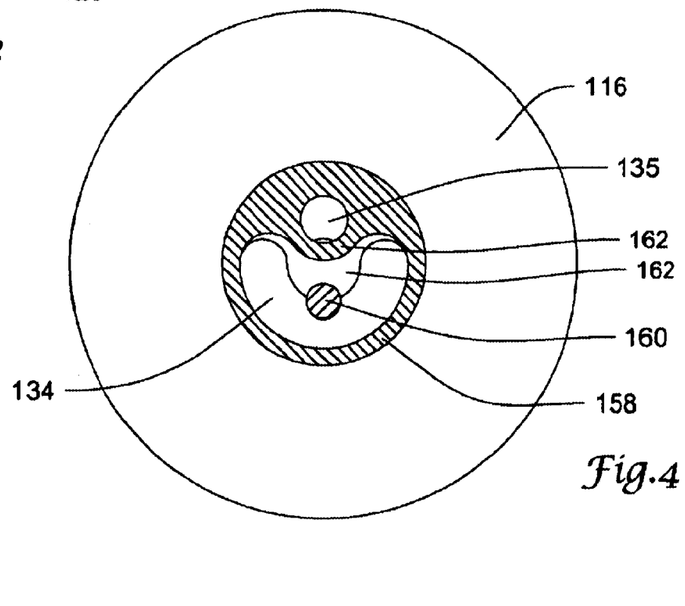
FIG. 4 is an axial cross-sectional view of another portion of the shaft of the catheter of FIG. 1, along line 4—4 of FIG. 1.

FIG. 3 shows an axial cross-sectional view of the catheter of FIG. 1, along line 3—3, looking towards the proximal end of catheter 110. The distal section of the catheter shaft 158 is dimpled in transition to the entry of the tube which creates the guide wire lumen 135 in FIG. 1. The distal stiffening wire 160 is shown approximately in the center of the lumen remaining. FIG. 4 shows another axial cross-sectional view of the catheter of FIG. 1, along line 4—4, looking towards the distal end of catheter 110. The guide wire lumen 135 is disposed over distal stiffening member 160 and inflation lumen 134. In production of a catheter of this embodiment of the present invention, the guide wire lumen 135 may be created by the integration of a guide wire tube 162 into the distal section of catheter shaft 158, for example by fusing the guide wire tube 162 into the distal section of catheter shaft 158 using heat shrink tubing (not depicted) and applying heat to the catheter shaft 158 wrapped in heat shrink tubing.

In a preferred embodiment, the distal flexible segment 158, together with any distal stiffening member 160, extends distally from a metallic tube section 126 to the other components, if any, at the distal end of the catheter. For example, a balloon 116 may be disposed adjacent the distal end of a distal flexible segment 158. In an exemplary embodiment, the third tubular segment 158 is a thermoplastic, such as polyether block amide. One example of such a material is PEBAX, which is available from Elf Autochem North America, of Philadelphia, Pa.

The polymeric tube 158 and stiffening wire 160, and metallic tube 126 if included, provide the necessary pushability for the catheter to permit its highly controlled advancement along a guide wire. The flexible distal portions of the catheter permit the catheter to negotiate the often tortuous vascular lumens, and the distal guide wire lumen 135 allows the catheter to be used in conjunction with a guide wire which has already established a path to that area of the vascular system of interest. Although the preceding description of the invention is directed to a balloon catheter, it will be appreciated by those skilled in the art that the invention may be used on other interventional catheters with lumenal or vascular interoperative devices using a core member, such as atherectomy devices, ultrasonic imaging and therapeutic catheters, laser catheters, stent delivery catheters, and perfusion catheters.

Figure 5:
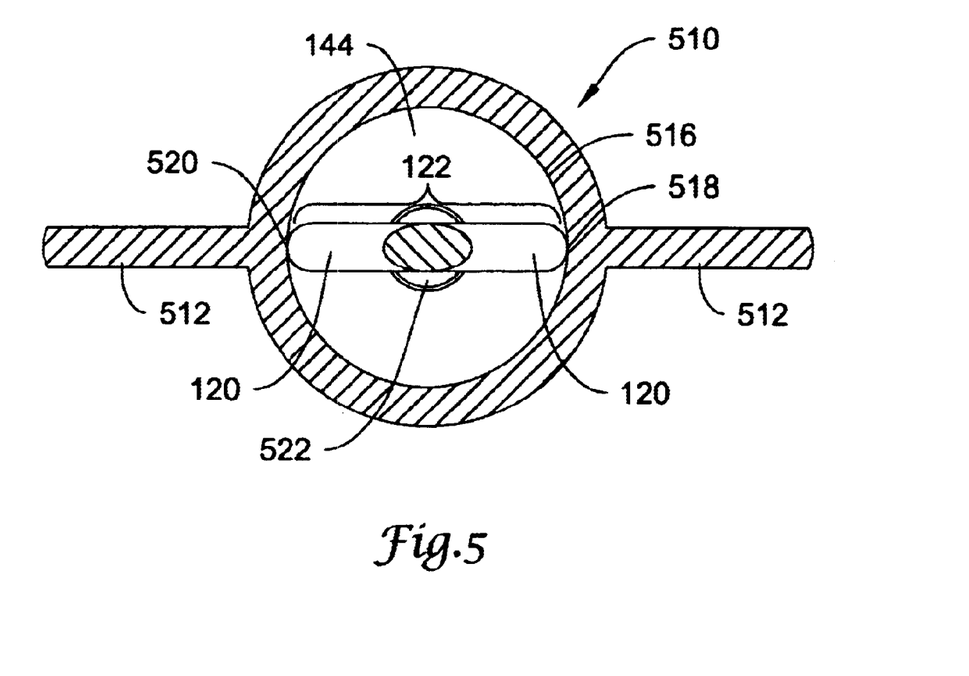
FIG. 5 is an axial cross-sectional view of the proximal (hub) portion of the catheter of FIG. 1, along line 5—5 of FIG. 1.
Figure 6:
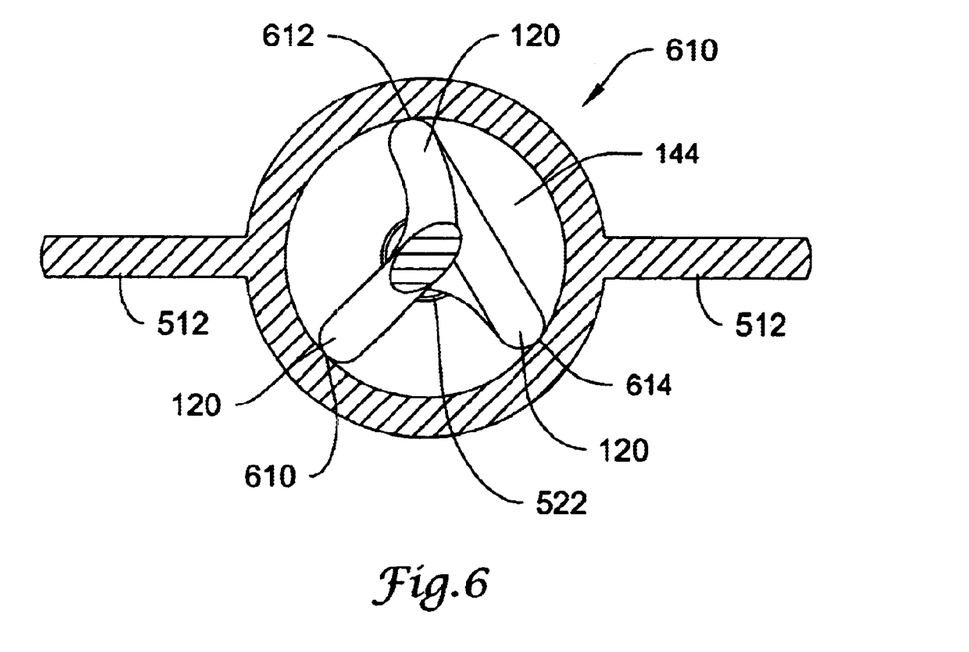
FIG. 6 is an axial cross-sectional view of the proximal (hub) portion of an alternate embodiment of the present invention, the cross section also corresponding to line 5—5 of FIG. 1.

In a preferred embodiment of the invention, the zigzag pattern of the core wire anchor 122 of FIG. 1 is executed approximately on a single plane, as depicted in FIG. 5, a cross-sectional view of the catheter of FIG. 1, cut along line 5—5 in FIG. 1. FIG. 5 shows an axial cross-sectional view of the core wire of one embodiment of the present invention. The cross-section of the hub 114 is shown generally at 510. The hub 510 consists of lateral wings 512, to aid in manipulation of the catheter, and a central lumen 144 defined by a hub wall 516. While the core member anchor 122 passes through the center of the catheter lumen 144, the core member 120 first approaches and contacts the hub inner wall at 518 while moving distally through the hub lumen 144. The core member 120 then changes direction, and after passing through approximately the center of the hub lumen 144, continues toward the opposite inner wall of the hub lumen 144, finally contacting the hub lumen inner wall at point 520. The core member 120 may then change direction again, contacting the opposite wall of the hub lumen 144, or moving approximately to the center of the hub lumen 144 prior to continuing into the catheter shaft lumen 522. While FIG. 5 shows a core member anchor 122 that subsists approximately in a single plane, other configurations that afford contact between the core member anchor 122 and the hub lumen 144 inner wall are possible within the scope of the invention. An example of an alternate configuration is depicted in FIG. 6. The hub is substantially identical to the hub depicted in FIG. 5, and is shown generally at 610. The core member 120, as it moves distally through hub lumen 144, follows an eccentric zigzag pattern that does not confine itself to a plane as the core member shown in FIG. 5, but rather contacts the inner wall of the hub lumen 144 along various longitudinal axes. For example, as depicted in FIG. 6, while crossing substantially over the center of the hub lumen at the plane of the cross-sectional view, the core member 120, while proceeding distally through the hub lumen, may cross the hub lumen so as to contact the hub lumen wall at point 610. Moving distally along the core member 120, the core member 120 may then traverse the hub lumen 144 so as to contact the inner wall of the hub lumen at point 612. The core member 120 may then cross the hub lumen at an angle so as to not pass through the central axis of the hub lumen 144, contacting the inner wall of the hub lumen again at point 614. Finally, in the embodiment of the present invention shown in FIG. 6, the core member 120 is angled so as to pass the central axis of the hub lumen 144, turning and entering catheter lumen 522. Alternatively, core member 120 may be formed into a helix pattern which may contact the inner wall of hub lumen 144 more or less continuously along a length of the core member. This embodiment of the present invention may be manufactured by initially forming the core member 120 into a coil or helix shape in the area of the core member anchor 122. This coil or helix may initially have a radial diameter greater than that of the hub lumen 144. The proximal tip 138 of the core member may then be used to twist the core member anchor 122 into a tighter coil or helix, thus reducing the diameter of the helix so that it may be fit within the hub lumen. Upon release of proximal tip 138, the coil is allowed to unwind or spring back toward its earlier larger diameter, until the inner wall of hub lumen 144, which circumscribes the coil or helix, is contacted. In this way, the core member anchor 122 will contact the inner wall of hub lumen 144 more or less continuously for a substantial portion of its length.

Alternatively, the core member 120 may be formed from a material with a shape memory, and be placed in the hub in a compressed state, expanding under conditions differing from those of initial placement which cause the coil formed in the core member to expand.

Although the present invention has been described with reference to preferred embodiments, workers skilled in the art will recognize that changes may be made in form and detail without departing from the spirit and scope of the invention.

What is claimed is:

1. A catheter, comprising:

an elongate flexible tubular shaft having a proximal end and a distal end, and defining a lumen therein;

a hub attached to the proximal end of the shaft, defining a lumen therein, the hub lumen having an inner wall;

a core member disposed at least in part within the hub lumen, the core member having a proximal end and a distal end, and having a proximal tip and a distal tip;

the core member being formed at the proximal end of the core member into a helix pattern biased to expand so that the core member contacts the inner wall of the hub along a length of the core member, with force sufficient to cause the retention of the core member in the hub in a substantially fixed position relative to the hub.

2. A catheter as defined in claim 1, wherein the hub lumen is in fluid communication with the shaft lumen.

3. A catheter as defined in claim 1, wherein a flexible strain relief surrounds the shaft proximate and distal to said hub.

4. A catheter as defined in claim 1, wherein the helix is a conical helix.

5. A catheter as defined in claim 1, wherein the helix is a cylindrical helix.

6. A catheter as defined in claim 1, wherein the proximal tip of the core member is shaped to form a plane which is not perpendicular to the radial axis of the proximal end of the core member.

7. A catheter as defined in claim 1, wherein the proximal tip of the core member is pointed.

8. A catheter, comprising:

an elongate flexible tubular shaft having a proximal end and a distal end, and defining a lumen, therein;

a hub attached to the proximal end of the shaft, defining a lumen therein, the hub lumen having an inner wall;

a core member disposed at least in part within the hub lumen;

the core member being formed at the proximal end of the core member into a pattern which traverses the hub lumen to contact the inner wall of the hub at two or more points with force sufficient to cause the retention of the core member in the hub in a substantially fixed position relative to the hub and configured such that at least two of the points of the core member and the central longitudinal axis of the hub lumen are not coplanar.

9. A catheter as defined in claim 8, wherein the hub lumen is in fluid communication with the shaft lumen.

10. A catheter as defined in claim 8, wherein a flexible strain relief surrounds the shaft proximate and distal to said hub.

11. A catheter as defined in claim 8, wherein the core member traverses the lumen of the hub in a substantially planar fashion.

12. A catheter as defined in claim 8, wherein the points of contact between the core member and the inner wall of the hub lie on at least two separate longitudinal axes of the inner wall.

13. A catheter as defined in claim 8, wherein the points of contact between the core member and the inner wall of the hub each lie on a longitudinal axis of the hub different from the longitudinal axis on which lies any other point of contact between the core member and the inner wall of the hub.

14. A catheter as defined in claim 8, wherein the proximal tip of the core member is shaped to form a plane which is not perpendicular to the radial axis of the proximal end of the core member.

15. A catheter as defined in claim 8, wherein the proximal tip of the core member is pointed.

* * * * *